United States Patent [19]

Malinowski

[11] 4,144,459

[45] Mar. 13, 1979

[54] SMOKE DETECTOR WITH TEST MEANS FOR SIMULATING A PREDETERMINED PERCENTAGE OF SMOKE

[75] Inventor: William J. Malinowski, Pembroke, Mass.

[73] Assignee: Chloride Incorporated, Tampa, Fla.

[21] Appl. No.: 855,624

[22] Filed: Nov. 29, 1977

[51] Int. Cl.$^2$ ............................................. G01N 21/26
[52] U.S. Cl. ...................................... 250/574; 340/515
[58] Field of Search ................ 340/515, 630; 250/573, 250/574, 575; 356/208

[56] References Cited

U.S. PATENT DOCUMENTS

| | | | |
|---|---|---|---|
| 3,868,184 | 2/1975 | Marsocci | 250/574 |
| 4,053,785 | 10/1977 | Lee et al. | 340/515 |

*Primary Examiner*—David C. Nelms
*Attorney, Agent, or Firm*—Robert E. Ross

[57] ABSTRACT

A smoke detector of the photo-electric type having a photo-responsive device viewing a volume illuminated by a light beam, in which a test member is provided for being temporarily positioned in the light beam so that one side of said member is exposed to the light and the other side is in the view of the photo-responsive device.

The test member has a translucent area at the forward edge which is small in relation to the cross-sectional area of the light beam. The translucent area illuminated by the beam simulates a pre-determined percentage of smoke in the beam with a high degree of accuracy since the transmission characteristics of the translucent area can be consistently maintained within production tolerances, and the exact position of the translucent area in the light beam for the smoke simulation is not critical.

8 Claims, 7 Drawing Figures

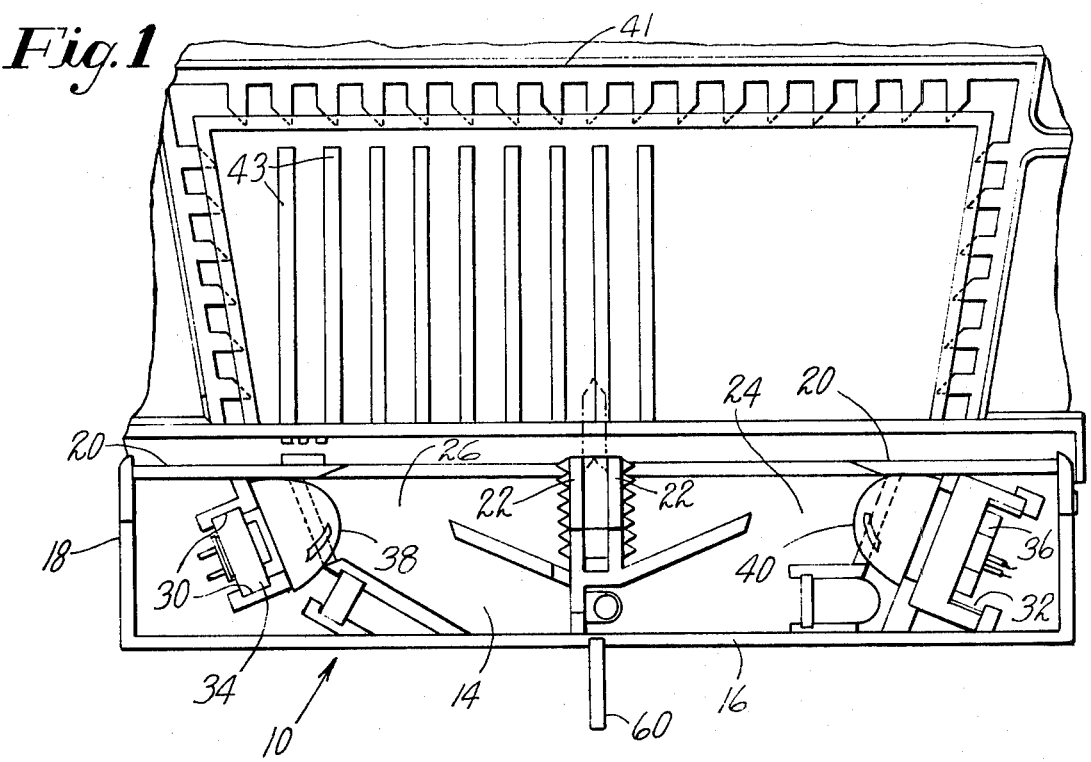

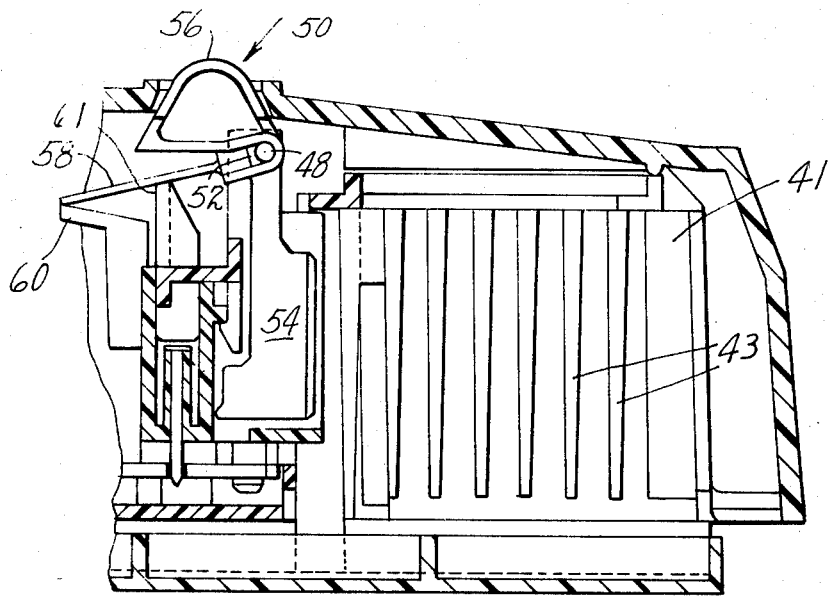
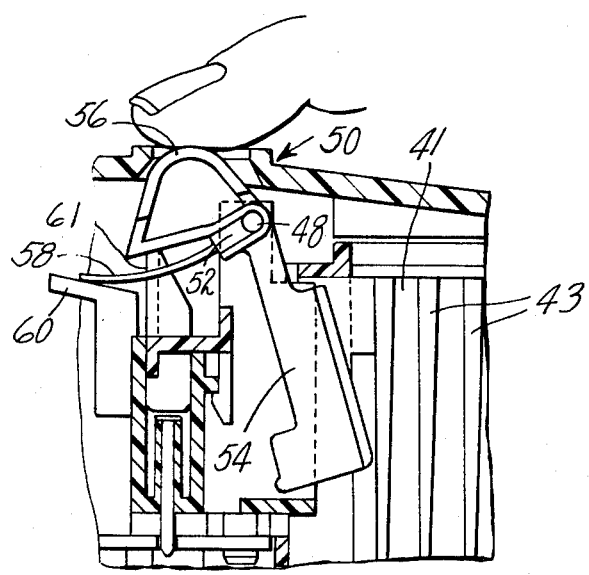

4,144,459

SMOKE DETECTOR WITH TEST MEANS FOR SIMULATING A PREDETERMINED PERCENTAGE OF SMOKE

BACKGROUND OF THE INVENTION

Smoke detectors of the photo-electric type utilize a focused light beam passing through a volume which receives smoke from the ambient atmosphere, with a photo-responsive device viewing the light beam at an angle to the axis thereof, so that smoke particles illuminated by the beam are seen by the photo-responsive device.

Such detectors are calibrated to provide an alarm when the concentration of smoke in the light beam reaches a predetermined level. Certain organizations that test and approve smoke detectors require that means be provided whereby the user of the detector can test the operability thereof, by simulating the amount of smoke to which the detector is required to respond.

Various methods have been proposed to provide such test means. However, it has been found difficult to provide a method which will give consistent results in a smoke detector manufactured in great quantity because of the difficulty of holding accurate tolerances in the mechanical components. Methods used heretofore depend on light reflected or scattered from an object, such as a wire, inserted into the light beam. However, the amount of light scattered onto the cell depends on the size of the wire, the surface finish thereof, and its position in the light beam. The diameter of the wire required to provide the small amount of light required is very small, and is therefore susceptible to damage in handling during manufacture or damage in use by the user.

SUMMARY OF THE INVENTION

This invention provides a test member for positioning in the light beam so that one side thereof is illuminated by the light source and the other side thereof is in the view of the photo-responsive device. At least a portion of the front edge of the test member is translucent, said translucent portion being small in area in relation to the cross-sectional area of the portion of the light beam into which it is inserted.

In one commercial embodiment of the invention, the test member is positioned in a slot in the housing containing the light source and photo-cell, and operable by an external lever to be moved out of the slot so that the leading edge of the test member enters the light beam. The leading edge may be beveled, so that the extreme forward edge thereof is thin enough to be translucent.

Hence, when the test member is projected forwardly into the light beam, the amount of illuminated edge seen by the photo-cell will be consistent from one detector to another so long as the forward edge of the test member is positioned within about the center one quarter of the light beam. The dimensional tolerances of the mechanical components necessary to position the test member in the test position are therefore not restrictive.

BRIEF DESCRIPTION OF THE DRAWINGS

FIG. 1 is a top plan view, partly broken away, showing a housing for the optical components of a smoke detector with the cover removed.

FIG. 2 is a view of the housing of FIG. 1 as seen from the front, with the cover in place.

FIG. 3 is a view in section taken on line 3—3 of FIG. 2, with the test member in the normal retracted position.

FIG. 4 is a view similar to FIG. 3 in which the test member is in the forward or test position.

DESCRIPTION OF THE ILLUSTRATED EMBODIMENT

Figure 5:
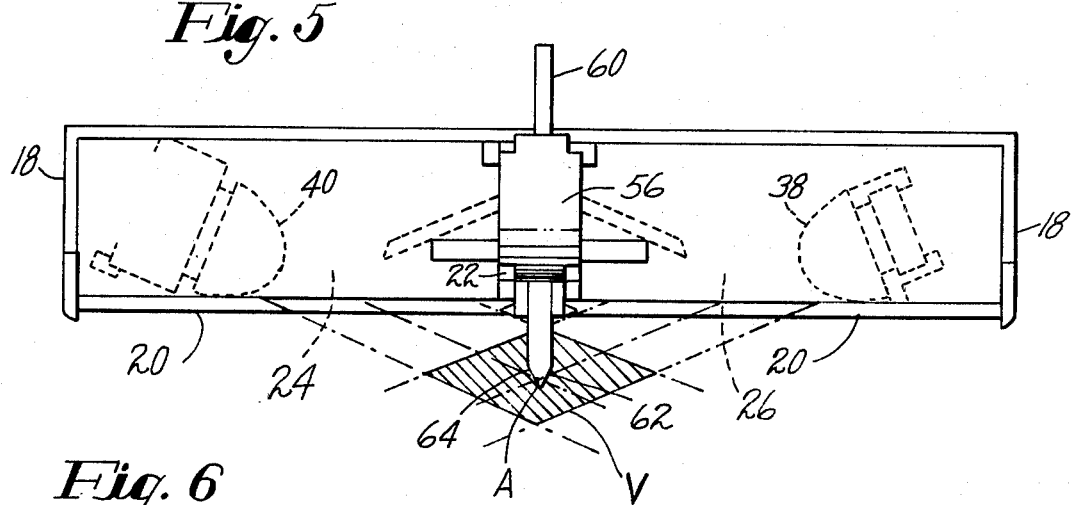
FIG. 5 is a top plan view of FIG. 4.

Referring to the drawing, there is illustrated a housing 10 for use in a smoke detector of the photo-electric type. The housing is preferably formed of injection molded plastic and comprises a body 12 comprising a base 14, a back wall 16, end walls 18, front wall portions 20 and a pair of upstanding members 22 medially disposed between the ends of the front walls, forming openings 24 and 26 between said upstanding members and the adjacent ends of the wall portions 20. The upstanding members 22 are spaced apart forming a slot 28.

Other upwardly extending members are provided in the housing to form suitably shaped cavities 30 and 32 to receive respectively a light source 34 and a photo-responsive device 36, with associated housing lenses 38 and 40.

The cavities 30 and 32 are shaped and dimensioned to retain the light source and photo-responsive device in a position and orientation such that the light beam from the source projects out of the opening 26 at an angle of about $22\frac{1}{2}°$ from the longitudinal axis of the housing and the viewing axis of the photo-responsive device extends out of the opening 24 also at an angle of about $22\frac{1}{2}°$ to the axis of the housing, so that the viewing axis of the photo-responsive device intersects the axis of the light beam in front of the medial portion of the housing at a point A (FIG. 5) at an angle of about 135° to take advantage of the well-known "forward scatter" effect. The intersection of the viewing cone of the photo-cell and the cone of the light beam is illustrated by the shaded area.

The viewing area of the photo-cell may be surrounded by a suitable enclosure 41 having internal light absorbing baffles 43, said enclosure having suitable apertures (not shown) to freely admit ambient atmosphere.

The light source and photo-responsive device may be connected into suitable circuitry (not shown), by which the light source is energized in a desired manner, and light reflected onto the photo-responsive device from smoke particles in the light beam cause a response of said photo-responsive device that actuates an alarm.

Examples of such circuitry may be found in my U.S. Pat. Nos. 3,946,241 issued Mar. 23, 1976, 3,917,956 issued Nov. 4, 1975, and my co-pending application Ser. No. 815,103 filed July 13, 1977.

A cover plate 42 is provided for the housing, said plate being provided with an aperture 44 in the medial portion of the front edge and a pair of support arms 46 extending upwardly on opposite sides of the aperture, each leg having an inwardly extending pin 48 near the upper end thereof.

Assembled with the cover is a test lever 50, comprising a medial portion having a pair of recesses 52 on opposite sides thereof receiving the pins 48 so that the lever is movable on said pins as an axis. Depending from the medial portion is a test member 54 which is disposed in the slot 28 of the housing, and extending upwardly and rearwardly therefrom is an operating member 56. Extending rearwardly from the lever 50 is an integral plastic leaf spring 58, which, when the lever and cover are assembled with the housing, rests on a spring support 60 on the rear of the housing, so that the lever is biased clockwise (as seen in FIG. 3) retaining the test plate 54 retracted into the slot 28.

The test plate 54 is moved to the test position by depressing the operating member 56, thereby pivoting the lever 50 counter-clockwise (FIG. 4) and flexing the spring 58.

To limit the pivoting movement of the lever, so that when the operating member is depressed the leading edge of the test plate stops substantially at the center of the light beam, stop member 6 is provided on the cover, positioned to contact the operating member 56 and limit the downward movement thereof.

Figure 7:
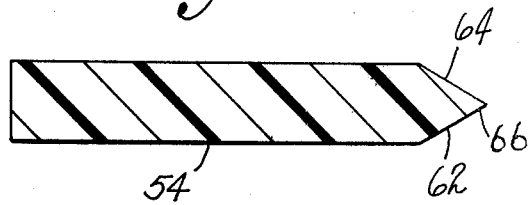
FIG. 7 is a view in section taken on line 7—7 of FIG. 6.
Figure 6:
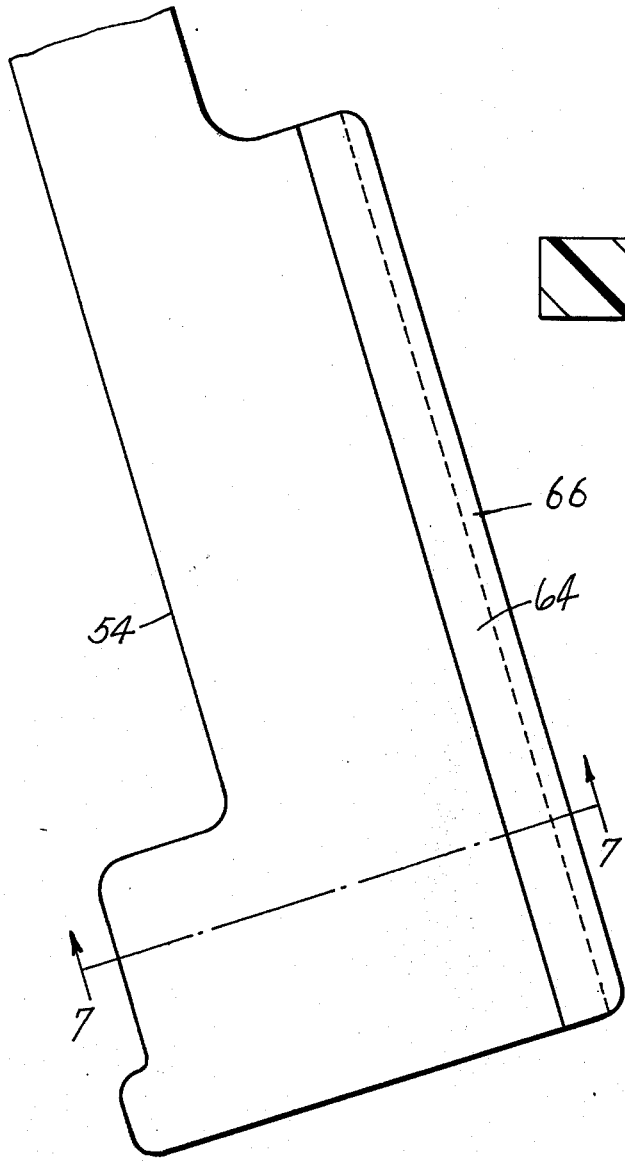
FIG. 6 is an enlarged view of the test member as seen in FIG. 4, with the translucent portion of the forward edge being indicated.

As illustrated in FIGS. 6 and 7, the leading portion of the test plate is V-shaped, with a small radius on the extreme front edge. When the test plate is moved forwardly into the light beam, one side thereof is illuminated by the light beam, and the other side is viewed by the photo-responsive device. In a preferred embodiment of the invention the housing 10 and the lever 50 are formed of black plastic, to absorb stray radiation and to minimize the transmission of light through the test plate 54.

However, it has been found that if the test plate is made thick enough so that substantially no light passes therethrough, and is given a beveled front edge, forming surfaces 62 and 64 disposed at a predetermined angle, sufficient light is transmitted through the thin section 66 at the extreme forward edge of the beveled portion and seen by the photo-responsive device to simulate the required amount of smoke and actuate the alarm.

The amount of light passing through the forward end of the beveled portion of the test plate for a given plastic composition, is a function of the included angle between the two surfaces and the length thereof exposed to the light and seen by the photo-responsive device with a greater light transmission resulting with smaller angles. For a detector housing of given size and composition, the bevel angle between the surfaces that will simulate a required amount of smoke can easily be determined by experiment.

Since changes apparent to one skilled in the art may be made in the illustrated embodiment of the invention without departing from the scope of the invention, it is intended that all matter contained herein be interpreted in an illustrative and not a limiting sense.

I claim:

1. In a smoke detector of the photo-electric type which includes a light source providing a light beam and photo-responsive means viewing transversely a portion of the light beam, the improvement comprising test means for simulating a predetermined percentage of smoke, said means comprising a member having a translucent portion at the extreme forward edge, and means for temporarily positioning the member in the light beam between the light source and the photo-responsive device so that the translucent portion is illuminated on one side by the light beam and the other side is viewed by the photo-responsive device.

2. A smoke detector as set out in claim 1 in which said test member comprises a plate formed of a material, and the main body thereof having a thickness, such that the main body of said plate is opaque, and having a thinner portion at the extreme forward edge, and means for temporarily positioning the plate so that the forward edge of the plate extends across substantially the medial portion of the light beam.

3. A smoke detector as set out in claim 2 in which said forward edge is beveled to provide an increasing thickness from the extreme front edge.

4. A housing for the optical components smoke detector of the photo-electric type, said housing comprising means retaining and positioning a light source and a photo-responsive device so that the light beam from the light source and the field of view of the photo-cell intersect outside of the housing, and a test member carried by the housing and temporarily movable into a test position at the intersection of the light beam and field of view of the photo-responsive device, said test means having a translucent forward edge portion which, when the test means is moved into the test position, is illuminated on one side by the light source and the other side is viewed by the photo-responsive device.

5. A housing as set forth in claim 4 in which the test means is an opaque plate having a forward edge which is of reduced thickness so as to be translucent and positioning means is provided which is dimensioned and positioned to stop said edge in the medial portion of the light beam when the plate is moved into the test position.

6. A housing for the optical components of a smoke detector of the photoelectric type, comprising an elongated box having openings in the front side thereof and internal means for retaining a light source in one end and a photo-responsive device in the other end so positioned that the light beam from the light source and the field of view of the photo-responsive device pass through said openings and intersect in front of the box, and a test member mounted on the box intermediate the light source and photo-responsive device, said test member being movable forwardly into a test position from the housing into the volume of intersection of the light beam and photo-responsive field of viewing, and having a light transmitting portion which, when the test member is in the test position, is illuminated on one side by the light beam and the other side is viewed by the photo-responsive device.

7. A housing as set forth in claim 6 in which slot means is provided between the light source and the photo-responsive device, said test member is normally disposed in the slot, said plate being so mounted in the housing as to be movable forwardly out of the slot so that the light transmitting portion thereof is centrally positioned between the light source and the photo-responsive device with one side being illuminated by the light source and the other side being viewed by the photo-responsive device.

8. A housing as set forth in claim 6 in which the axis of the light beam and the axis of field of view of the photo-responsive device intersect in front of the box at an angle of between about 90° and 150°, and said test member is so mounted as to be positioned in the area of intersection of said light beam and field of view of said photo-cell when moved into the test position.

* * * * *